United States Patent
Yasuhara et al.

(10) Patent No.: US 6,562,244 B1
(45) Date of Patent: May 13, 2003

(54) METHOD AND APPARATUS FOR DISINFECTING DRAINAGE

(75) Inventors: Yoshiharu Yasuhara, Tokyo (JP); Kazuhiro Hasegawa, Tokyo (JP); Kazunari Tanaka, Tokyo (JP); Yuichi Fuchu, Tokyo (JP); Yutaka Niida, Tokyo (JP); Hideyuki Yoshida, Tokyo (JP); Hiromasa Kaihatsu, Tokyo (JP); Hiroshi Toriumi, Tokyo (JP); Hiroshi Takasu, Tokyo (JP); Tadashi Nagawa, Tokyo (JP); Sumio Komine, Tokyo (JP)

(73) Assignee: Ebara Corporation, Tokyo (JP)

( * ) Notice: Subject to any disclaimer, the term of this patent is extended or adjusted under 35 U.S.C. 154(b) by 0 days.

(21) Appl. No.: 09/787,896

(22) PCT Filed: Sep. 27, 1999

(86) PCT No.: PCT/JP99/05233

§ 371 (c)(1),
(2), (4) Date: Mar. 28, 2001

(87) PCT Pub. No.: WO00/18689

PCT Pub. Date: Apr. 6, 2000

(30) Foreign Application Priority Data

Sep. 28, 1998 (JP) .......................................... 10-273746

(51) Int. Cl.[7] ................................................. C02F 1/50
(52) U.S. Cl. ................... 210/755; 210/764; 210/198.1; 210/209
(58) Field of Search ................................ 210/754, 755, 210/764, 747, 170, 198.1, 209, 908

(56) References Cited

U.S. PATENT DOCUMENTS

| | | | |
|---|---|---|---|
| 3,412,021 A | | 11/1968 | Paterson |
| 5,037,541 A | * | 8/1991 | Ruey-Jang et al. |
| 5,294,337 A | * | 3/1994 | Johnson |
| 5,422,126 A | | 6/1995 | Howarth et al. |
| 5,759,415 A | * | 6/1998 | Adams |

FOREIGN PATENT DOCUMENTS

| | | |
|---|---|---|
| CA | 2 042 430 | 11/1991 |
| JP | A-55-24514 | 2/1980 |
| JP | 55-024514 | 2/1980 |
| JP | 05-154462 | 6/1993 |
| JP | A-5-154462 | 6/1993 |
| JP | 05-309207 | 11/1993 |
| JP | A-5-309207 | 11/1993 |
| JP | A-7-68248 | 3/1995 |
| JP | 07-068248 | 3/1995 |
| JP | A-8-176996 | 7/1996 |
| JP | 08-176996 | 7/1996 |
| JP | 8-508230 | 9/1996 |
| JP | 09-122656 | 5/1997 |
| JP | A-9-122656 | 5/1997 |
| WO | WO 94/21125 | 9/1994 |

OTHER PUBLICATIONS

Derwent Abstracts, Accession No. 1978–13432A, SU 263 487, Apr. 28, 1977.
Patent Abstracts of Japan, vol. 1995, No. 8, Sep. 29, 1995, JP 07–132299, May 23, 1995.

* cited by examiner

Primary Examiner—Betsey Morrison Hoey
(74) Attorney, Agent, or Firm—Oblon, Spivak, McClelland, Maier & Neustadt, P.C.

(57) ABSTRACT

A method and an apparatus for disinfecting drainage are provided. A bromine-based or iodine-based disinfectant is added to water to obtain disinfecting water, and the disinfecting water is added to predetermined drainage. The apparatus has a device for producing disinfecting water from a disinfectant and drainage, a sand basin, and a channel for introducing the disinfecting water into the sand basin, and the drainage is disinfected while the drainage is dwelling in the sand basin.

21 Claims, 2 Drawing Sheets

METHOD AND APPARATUS FOR DISINFECTING DRAINAGE

TECHNICAL FIELD OF THE INVENTION

The present invention relates to a method and an apparatus for disinfecting drainage, and more particularly, to a method and an apparatus for disinfecting sewage diluted with rainwater.

RELATED ART

In sewage works, sewage is subjected to treatment in a sand basin for removing sand, etc., solid-liquid separation for removing suspended solids (SS), activated sludge treatment, and disinfection in this order, and then discharged to public waters such as rivers, lakes, ports, and coastal waters.

Disinfection generally involves the use of a chlorine gas or a chlorine-based disinfectant, because sewage, night soil, industrial drainage, etc. may contain pathogens which cause infectious diseases. Generally, the chlorine-based disinfectant is added to such drainage to be treated, thereby decreasing the number of coliform organisms (coliform organism count) to 3,000 CFU (colony forming unit)/ml or less. CFU refers to a colony forming unit. Alternatively, ultraviolet irradiation or ozonization may be performed without the addition of the chlorine-based disinfectant. Since such a technique requires vast equipment, however, its applications are limited.

A combined sewer is a system for collecting household waste water, industrial drainage, and rainwater into the same pipe, and sending the combined water to sewage works, where the aforementioned treatments are carried out. When there is much rainfall, rainwater-incorporating sewage in excess of the amount that can be treated at sewage works is likely to flow into the sewage works. Thus, discharge takes place from (wet-weather) sewage removal facilities, such as a storm outflow and pump station, to public waters. Recently, techniques for preventing overflow of bulky waste, floating matter, etc. by providing sewage removal facilities with screens have begun to be studied to protect the scenery of public waters such as rivers. However, no studies have been performed on techniques for disinfecting coliform organisms included at a count of several tens of thousands to several hundreds of thousands in water discharged from sewage removal facilities.

A separated sewer is a system for collecting both of household waste water and industrial drainage, and rainwater into different pipes, and sending the household waste water and industrial drainage to sewage works, while discharging the rainwater as an overflow. The separated sewer overflow should essentially comprise only rainwater. Actually, however, when much rain falls, a large amount of rainwater flows in the sewer. On this occasion, pollutants present on ground surfaces, such as roads, and sludge deposited in the sewer are flowed together. Thus, the separated sewer overflow also contains *Escherichia coli* ascribed to the pollutants existent on ground surfaces and the sludge. In each case, the coliform organism count in the overflow may exceed the discharge control value (3,000 CFU/ml or less). In this case, disinfection is desired.

Chlorine-based disinfectants have many advantages, such that the equipment used is simple, and their applicability to any state of dirt is high, compared with ultraviolet irradiation and ozone sterilization.

However, when the techniques applied to ordinary sewage treatment are diverted to disinfection of combined sewer overflow, the following problems arise: In sewage in rainy weather, ammonia or amine is coexistent. Thus, a chemical reaction typified by the chemical equation (1) indicated below takes place. As a result, active chlorine is converted to chloramine, decreasing a microbicidal effect to one-tenth or lower. Hence, in the presence of ammonia or amine, the amount of the chlorine-based disinfectant added needs to be increased, even if the pathogen count is unchanged.

$$NH_4^+ + HClO \rightarrow NH_2Cl + H_2O + H^+ \qquad (1)$$

The disinfection time for the use of the chlorine-based disinfectant is required to be 15 minutes or more (see "Sewer Facilities—Plan & Design Guidelines and Description"). Thus, there is need for a mixing tank in which sewage in rainy weather and the chlorine-based disinfectant are mixed and caused to dwell for 15 minutes or more. However, the (wet-weather) sewage removal facilities have no ample space where such a mixing tank can be installed.

Thus, a disinfectant taking a short disinfection time, and a method for mixing it are required of disinfection of combined sewer overflow.

J. E. Alleman, J. E. Etzel, D. E. Gendron, J. C. Conley, W. F. McCoy, and A. J. Hein, Bromine-Based Disinfection Performance, a paper by researchers of Purdue University and Great Lakes Chemical Company, reports on laboratory-scale experiments in which bromine chloride (BrCl), bromine ($Br_2$), and bromochlorodimethylhydantoin (BCDMH) were each added to dummy drainage containing bacteria such as coliform bacilli. As the dummy drainage, water at pH 7.2 containing a low concentration of ammonia (2 mg/L), or water at pH 8.2 containing a high concentration of ammonia (20 mg/L) was used. As the bacteria, *Escherichia coli*, Pseudomonas, and *Streptococcus faecalis* were used. However, the paper does not describe the dummy drainage as containing organic matter.

Japanese Unexamined Patent Publication No. 4-156994 describes a method of pouring a germicide into cooling water. As regards the germicide, the formation of hypobromite ions by a redox reaction between ozone and bromine ions is described. However, the cooling water contains no ammonia.

Japanese Unexamined Patent Publication No. 11-47755 describes a slime control agent containing a hydantoin compound as an active ingredient, and a slime control method using such an agent. The slime control agent is used in storage water for use at a pulp plant or a paper making factory.

SUMMARY OF THE INVENTION

According to an aspect of the present invention, there is provided a method for disinfecting drainage, comprising the steps of mixing a disinfectant, which can form HOX where X is a bromine atom or an iodine atom, and which contains a bromine atom or an iodine atom, with water to obtain disinfecting water; and adding the disinfecting water to the drainage containing organic matter and ammonia or ammonium ions to disinfect the drainage.

In the invention, the total organic carbon in the drainage is preferably 5 mg/liter or more. The ammonium ion concentration in the drainage is preferably 1 mg/liter or more.

The drainage preferably includes rainwater. The drainage also preferably includes sewage diluted with rainwater.

The disinfectant preferably contains a 4- to 10-membered heterocyclic ring which may be condensed with other ring and which contains 1 to 4 hetero-atoms comprising nitrogen atoms or sulfur atoms. The heterocyclic ring preferably includes a group of the formula —N(X)—C(=O)—, where X includes a bromine atom or an iodine atom, in a ring skeleton. Furthermore, it is preferred that the disinfectant be a solid, and the step of obtaining disinfecting water should include the step of dissolving the disinfectant in the drainage.

The concentration of the disinfectant in the disinfecting water is preferably 100 mg/liter as Cl to 10 g/liter as Cl calculated as an active chlorine concentration.

The concentration of the disinfectant added in the drainage is preferably 0.5 mg/liter as Cl to 25 mg/liter as Cl calculated as an active chlorine concentration.

The step of adding the disinfecting water preferably includes the step of introducing the disinfecting water below the water surface of the drainage. It is also preferred that the step of discharging the disinfected drainage to public waters be further included.

According to another aspect of the invention, there is provided an apparatus for disinfecting drainage, comprising a device for producing disinfecting water from a disinfectant and the drainage; a sand basin for removing sand in the drainage; and a first channel for introducing the disinfecting water into the sand basin, wherein the drainage is disinfected while the drainage is dwelling in the sand basin.

In the invention, the device for producing disinfecting water preferably has a disinfectant storing device, a device for adding the disinfectant to the drainage, and a device for mixing the disinfectant and the drainage. Preferably, the sand basin has two or more sand settling portions, and the first channel has a distribution tank for introducing the disinfecting water to each of the sand settling portions.

The first channel is preferably connected to an adding device for introducing the disinfecting water below the water surface of the drainage.

It is preferred that a reservoir for storage, or a discharge waterway be further included so that the disinfected drainage can be discharged to public waters.

The reservoir or the discharge waterway is preferably provided with a measuring instrument for inspecting the water quality of the disinfected drainage.

It is preferred that a second channel for introducing part of the drainage in the sand basin into the device for producing disinfecting water be further included.

Preferably, the above disinfectant can form HOX, where X is a bromine atom or an iodine atom, and contains a bromine atom or an iodine atom.

The disinfectant also preferably contains a 4- to 10-membered heterocyclic ring which may be condensed with other ring and which contains 1 to 4 hetero-atoms comprising nitrogen atoms or sulfur atoms.

PREFERRED EMBODIMENTS OF THE INVENTION

Figure 1:
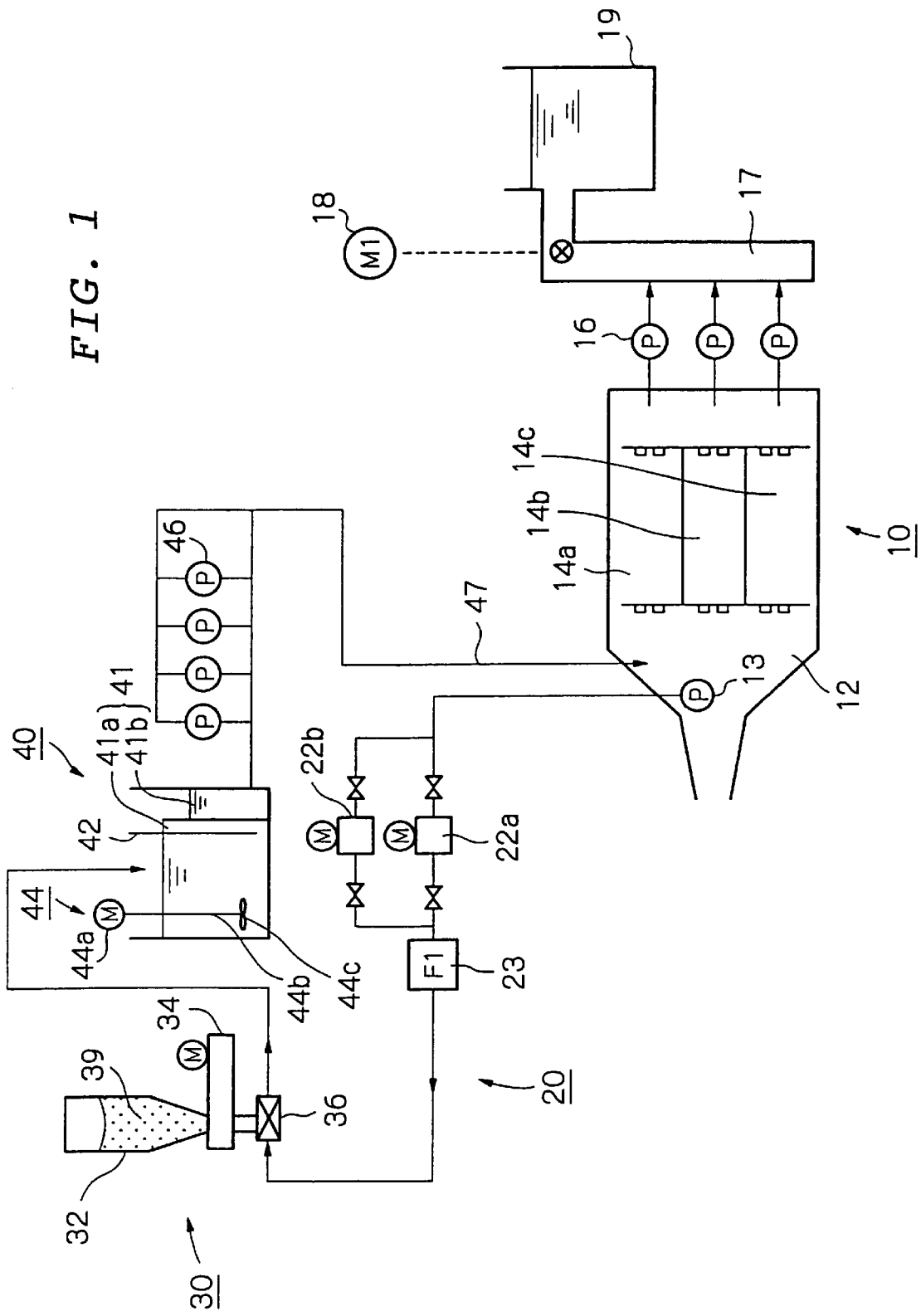
FIG. 1 is an explanatory view of an embodiment of an apparatus according to the present invention.

According to an aspect of the invention, drainage containing organic matter and ammonia or ammonium ions is disinfected.

In the combined sewer, for example, raw sewage and rainwater are mixed and flow. Such combined sewer overflow, especially, that which has not been treated at sewage works is disinfected by the method of the invention.

The separated sewer is a system in which a sewer for raw sewage and a sewer for rainwater are separated. According to this system, wet-weather sewage flowing in the rainwater sewer is disinfected by the method of the invention.

As the content of organic matter in drainage, for example, the total organic carbon in the drainage may be 5 mg/liter or more, 10 mg/liter or more, 30 mg/liter or more, or 50 mg/liter or more. In each of the combined type sewage and the separated type sewage, the total organic carbon is generally 5 mg/liter or more.

The ammonium ion concentration of the drainage may be 1 mg/liter or more, or 10 mg/liter or more. When ammonium ions are contained in the drainage, active bromine or active iodine changes into $NH_2X$ or $NHX_2$ where X denotes a bromine atom or an iodine atom. Bromoamine ($NH_2Br$), however, retains an disinfecting effect comparable to that of hypobromous acid, and is capable of effective disinfection. In the combined sewage, the ammonia ion concentration is generally 1 mg/liter or more. In the separated sewage, an overflow immediately after rainfall, called first flush, often has an ammonia ion concentration of 1 mg/liter or more.

According to the one aspect of the invention, the drainage mainly targeted is sewage diluted with rainwater, but may be rainwater in the separated sewer. Furthermore, water containing organic matter and ammonia or amine, such as sewage, night soil, industrial drainage, or water resulting after treatment of them, may be treated by the method of the invention.

According to the one aspect of the invention, the water to be treated contains *E. coli*, because disinfection is highly necessary for such water. The combined sewage generally contains *E. coli*, and the separated sewage often contains *E. coli*.

According to the one aspect of the invention, a disinfectant, which can form HOX where X is a bromine atom or an iodine atom, and which contains a bromine atom or an iodine atom, is used. Preferably, a disinfectant, which can form hypobromous acid (HOBr) and which contains a bromine atom, is used. Compared with a chlorine-based disinfectant, the above bromine-based disinfectant or iodine-based disinfectant is characterized by a short disinfection time. The bromine-based disinfectant, for example, is capable of disinfection in several tens of seconds to several minutes. A hypohalogenous acid (HOX where X is a bromine atom or an iodine atom) easily decomposes in nature, and there is no need to provide a device for breaking down a hypohalogenous acid remaining in drainage. With the chlorine-based disinfectant, on the other hand, active chlorine reacts with ammonia in sewage to form chloramine, decreasing germicidal activity. This makes it difficult to complete disinfection within a dwelling time in the (wet-weather) sewage removal facilities. Since chloramine is highly residual, moreover, a device for decomposing it needs to be provided.

Examples of the disinfectant preferably used in the invention are hydantoins, cyanuric acids, isothiazolones, ε-caprolactams, phthalimides, pyrrolidones, acridones, uracils, succinimides, barbituric acids, creatinines, dioxopiperazines, urazoles, glycine anhydrides, heptalactams, maleic acid hydrazides, maleimides, octalactams, and oxindoles.

The hydantoins are expressed, for example, by the formula (II):

(I) 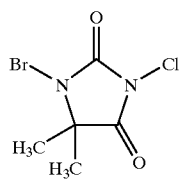

(II) 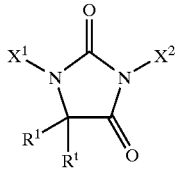

(III) 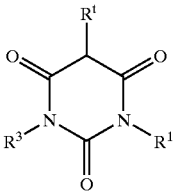

(IV) 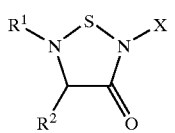

(V) 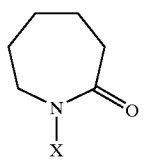

(VI) 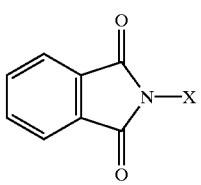

(VII) 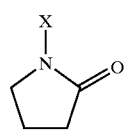

(VIII) 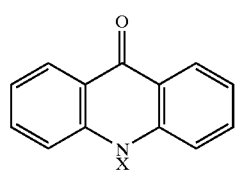

(IX) 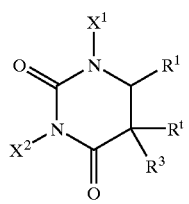

-continued (X) 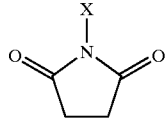

In the formula (II), $X^1$ and $X^2$ are the same or different, and are each independently a chlorine atom, a bromine atom, or an iodine atom, provided that one of $X^1$ and $X^2$ is a bromine atom or an iodine atom; and $R^1$ and $R^2$ are the same or different, and are each independently a hydrogen atom, or a lower alkyl group having 10 or less carbon atoms, preferably, a hydrogen atom, or a lower alkyl group having 6 or less carbon atoms, more preferably, a hydrogen atom, or a lower alkyl group having 3 or less carbon atoms.

As the hydantoin, 1-bromo-3-chloro-5,5-dimethylhydantoin (a compound of the formula (I)), for example, is named. Bromochlorodimethylhydantoin (BCDMH) is highly stable, and can maintain activity for several years if shielded from direct sunlight. BCDMH is a solid, and when dissociated, forms hypobromite ions, exhibiting a high disinfecting effect.

The cyanuric acids are shown, for example, by the formula (III) where $R^1$, $R^2$, and $R^3$ are the same or different, and are each independently a chlorine atom, a bromine atom, an iodine atom, a hydroxyl group, a hydrogen atom, or a lower alkyl group having 10 or less carbon atoms, provided that at least one of $R^1$, $R^2$, and $R^3$ is a bromine atom or an iodine atom; the lower alkyl group being preferably one having 6 or less carbon atoms, and more preferably one having 3 or less carbon atoms.

The isothiazolones are shown, for example, by the formula (IV) where

X is a bromine atom or an iodine atom;

$R^1$ and $R^2$ are the same or different, and are each independently a chlorine atom, a bromine atom, an iodine atom, a hydrogen atom, or a lower alkyl group having 10 or less carbon atoms, the lower alkyl group preferably having 6 or less carbon atoms, and more preferably having 3 or less carbon atoms.

A preferred example of the isothiazolone is 5-chloro-2-methyl-4-isothiazolin-3-one.

The ε-caprolactams are expressed, for example, by the formula (V) where X is a bromine atom or an iodine atom.

M The phthalimides are expressed, for example, by the formula (VI) where X is a bromine atom or an iodine atom.

The pyrrolidones are expressed, for example, by the formula (VII) where X is a bromine atom or an iodine atom.

The acridones are expressed, for example, by the formula (VIII) where X is a bromine atom or an iodine atom.

The uracils are expressed, for example, by the formula (IX) where $X^1$ and $X^2$ are the same or different, and are each independently a chlorine atom, a bromine atom, or an iodine atom, provided that one of $X^1$ and $X^2$ is a bromine atom or an iodine atom;

$R^1$ is a hydrogen atom, a lower alkyl group having 10 or less carbon atoms, an amino group, or a nitro group, the lower alkyl group preferably having 6 or less carbon atoms, and more preferably having 3 or less carbon atoms;

$R^2$ and $R^3$ are the same or different, and are each independently a hydrogen atom, or a lower alkyl group having 10 or less carbon atoms, preferably, a hydrogen atom, or a lower alkyl group having 6 or less carbon atoms, and more preferably a hydrogen atom, or a lower alkyl group having 3 or less carbon atoms.

The succinimides are expressed, for example, by the formula (X) where X is a bromine atom or an iodine atom.

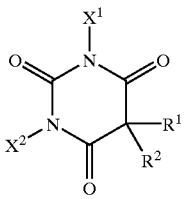

(XI)

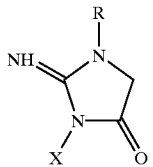

(XII)

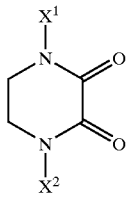

(XIII)

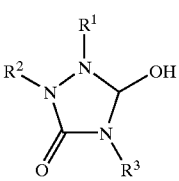

(XIV)

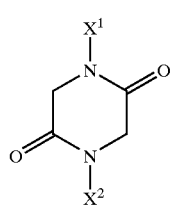

(XV)

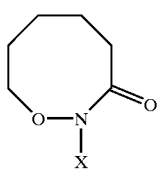

(XVI)

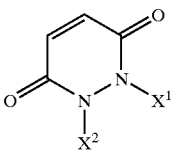

(XVII)

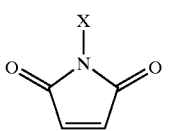

(XVIII)

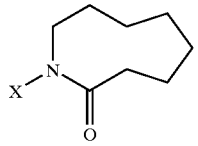

(XIX)

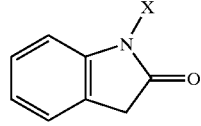

(XX)

The barbituric acids are expressed, for example, by the formula (XI) where $X^1$ and $X^2$ are the same or different, and are each independently a chlorine atom, a bromine atom, or an iodine atom, provided that one of $X^1$ and $X^2$ is a bromine atom or an iodine atom; and $R^1$ and $R^2$ are the same or different, and are each independently a hydrogen atom, or a lower alkyl group having 10 or less carbon atoms, preferably, a hydrogen atom, or a lower alkyl group having 6 or less carbon atoms, and more preferably a hydrogen atom, or a lower alkyl group having 3 or less carbon atoms.

The creatinines are expressed, for example, by the formula (XII) where

X is a bromine atom or an iodine atom; and

R is a hydrogen atom, or a lower alkyl group having 10 or less carbon atoms, preferably, a hydrogen atom, or a lower alkyl group having 6 or less carbon atoms, and more preferably a hydrogen atom, or a lower alkyl group having 3 or less carbon atoms.

The dioxopiperazines are expressed, for example, by the formula (XIII) where $X^1$ and $X^2$ are the same or different, and are each independently a chlorine atom, a bromine atom, or an iodine atom, provided that one of $X^1$ and $X^2$ is a bromine atom or an iodine atom.

The urazoles are expressed, for example, by the formula (XIV) where $X^1$ and $X^2$ are the same or different, and are each independently a chlorine atom, a bromine atom, or an iodine tom, provided that one of $X^1$ and $X^2$ is a bromine atom or an iodine atom; and $R^1$, $R^2$, and $R^3$ are the same or different, and are each independently a chlorine atom, a bromine atom, an iodine atom, a hydrogen atom, or a lower alkyl group having 10 or less carbon atoms, one of $R^1$, $R^2$, and $R^3$ being a bromine atom or an iodine atom, and the lower alkyl group preferably having 6 or less carbon atoms, and more preferably having 3 or less carbon atoms.

The glycine anhydrides are expressed, for example, by the formula (XV) where $X^1$ and $X^2$ are the same or different, and are each independently a chlorine atom, a bromine atom, an iodine atom, a hydrogen atom, or a lower alkyl group having 10 or less carbon atoms, one of $X^1$ and $X^2$ being a bromine atom or an iodine atom, and the lower alkyl group preferably having 6 or less carbon atoms, and more preferably having 3 or less carbon atoms.

The ω-heptalactams are expressed, for example, by the formula (XVI) where X is a bromine atom or an iodine atom.

The maleic acid hydrazides are expressed, for example, by the formula (XVII) where $X^1$ and $X^2$ are the same or different, and are each independently a chlorine atom, a bromine atom, or an iodine atom, provided that one of $X^1$ and $X^2$ is a bromine atom or an iodine atom.

The maleimides are expressed, for example, by the formula (XVIII) where X is a bromine atom or an iodine atom.

The octalactams are expressed, for example, by the formula (XIX) where X is a bromine atom organ iodine atom.

The oxindoles are expressed, for example, by the formula (XX) where X is a bromine atom or an iodine atom.

The disinfectant usable in the invention preferably contains a 4- to 10-membered heterocyclic ring, more preferably a 5- to 9-membered heterocyclic ring, containing nitrogen atoms or sulfur atoms, as shown by the formulas (I) to (XX). The heterocyclic ring preferably contains 1 to 4 hetero-atoms, more preferably 1 to 3 hetero-atoms. The hetero-atoms are nitrogen atoms or sulfur atoms.

The ring skeleton of the heterocyclic ring preferably includes a group of the formula —N(X)— where X is a chlorine atom, a bromine atom, or an iodine atom, preferably a bromine atom or an iodine atom, and more preferably a bromine atom.

As shown by the formula (XXI), the ring skeleton of the heterocyclic ring A, more preferably, includes a group of the formula —N(X)—C(=O)— where X is a bromine atom or an iodine atom. With this structure, a hypohalogenous acid is easily formed.

(XXI)

The heterocyclic ring may be condensed with other ring, for example, an aromatic ring such as a benzene ring, as shown by the formulas (VI), (VIII) and (XX).

According to the one aspect of the invention, the step of mixing a predetermined disinfectant with water is included. In the invention, the disinfectant may be added to drainage at the (wet-weather) sewage removal facilities. For example, the disinfectant may be added in the sewer pipe entering the (wet-weather) sewage removal facilities, or may be added in the sand basin, especially, the inflow portion of the sand basin. Alternatively, the disinfectant may be added in the rainwater removal pump well, or in the rainwater removal pump inflow pipe. That is, the disinfectant may be added in any of these places, and may be added at one site or at several sites.

Alternatively, the (wet-weather) sewage removal facilities may be provided with a main channel for flow of drainage, and a bypass channel branched from the main channel. In this bypass channel, a disinfection tank may be installed. In this disinfection tank, the disinfectant may be added to drainage, and dissolved therein.

The place of addition of the disinfectant is preferably on the entry side of the rainwater removal pump, because an agitating force in the pump mixes the disinfectant and the wet-weather sewage thoroughly. The addition of the disinfectant at the inflow portion of the sand basin is also preferred, because the dwell time in the sand basin can be utilized for the reaction time.

The disinfectant used in the invention is often a solid at room temperature. When a solid disinfectant is directly added to drainage, undissolved solids may be discharged along with the drainage, adversely affecting aquatic organisms in public waters. When the disinfectant is solid, therefore, it is preferred to dissolve the disinfectant in water to form disinfecting water, and add it to drainage. The method of dissolving is not restricted, and may be water jet agitation by an ejector, channel agitation, or a dissolving tank equipped with a mixer.

For example, there may be used disinfecting water having the disinfectant dissolved in an amount of 1% by weight or more, preferably 10% by weight or more, more preferably 20% by weight or more, based on the saturated solubility of the disinfectant. Needless to say, when the disinfectant is solid, not all of the disinfectant added needs to be dissolved in water, and instead, the solid-form disinfectant may remain in the disinfecting water.

Even when the disinfectant is a liquid at room temperature, on the other hand, the addition of a small amount of the liquid to a large amount of drainage takes some time until the liquid disinfectant and the drainage mix. In this case, they do not necessarily mix uniformly. Thus, it is preferred to add the disinfectant to water, and then add the resulting mixture to drainage.

The concentration of the disinfecting water is preferably 100 mg/liter as Cl to 10 g/liter as Cl, more preferably 200 mg/liter as Cl to 2 g/liter as Cl, calculated as the active chlorine concentration. If the concentration of the disinfecting water is lower than 100 mg/liter as Cl, the amount of the disinfecting water added may become large, and the disinfectant may be consumed due to solution, causing the risk of insufficient sterilization. If the concentration of the disinfecting water is higher than 10 g/liter as Cl, mixing of the disinfectant and the drainage will be insufficient, decreasing the disinfecting effect.

The amount of the disinfecting water added depends on the concentration of the disinfectant in the disinfecting water, the amount of rainfall, the water quality of drainage, etc. Generally, the amount of the disinfecting water added increases with the increase in the amount of rainfall, i.e., the amount of drainage, and the deterioration in the water quality. According to one embodiment of the invention, however, as rainwater increases, the turbidity, COD and $NH_4$ of incoming water decreases. Thus, even if rainwater increases and the amount of incoming water triples, there is no need to make the amount of addition of the disinfecting water or the disinfectant three-fold. Therefore, it would be rational to find the optimum amount of addition for the quality of incoming water by a beaker test or the like, and multiply this value by the amount of incoming water to determine the amount of the disinfecting water or the disinfectant added.

To know the quality of incoming water, it is advisable to measure its turbidity or electrical conductivity. By so doing, the state of incorporation of rainwater can be grasped. This indicator makes on-time detection possible. Other indicators usable are a rainfall pattern, properties of particles in wet-weather sewage, SS content, chemical oxygen demand (COD), and biological oxygen demand (BOD). These indicators may be combined arbitrarily. For the amount of incoming water, various flow meters may be utilized, but this amount may be determined by the number of the rainwater removal pumps in operation and the status of load on these pumps.

Then, the aforementioned disinfecting water is added to predetermined drainage to disinfect it. For example, the disinfecting water in a disinfecting water tank is introduced into the main channel via the bypass channel.

When the drainage is sewage, night soil, or industrial drainage, the concentration of the disinfectant added in the drainage is preferably 0.5 to 25 mg/liter as Cl, more preferably, 1 to 15 mg/liter as Cl, calculated as the active chlorine concentration. The concentration of the disinfectant added can be calculated from the concentration and amount of the disinfectant in the disinfecting water, as well as from the amount of the drainage. The concentration of the disinfectant added is the value present before the disinfectant is consumed in the drainage.

When the water to be treated is sewage, night soil, or industrial drainage, this water to be treated, generally, contains coliform bacilli in a range of $10^4$ to $10^7$ CFU/mL. However, the above amount of the disinfectant added can result in the sterilization of the water, which is to be treated, reliably and rapidly in a time of about 1 minute.

FIG. 1 is an explanatory view of an embodiment of a method according to the present invention.

Wet-weather sewage flows from the main channel into a sand basin 10. The sand basin 10 includes an inflow portion 12, and sand settling portions 14a, 14b, 14c arranged parallel to each other. The wet-weather sewage can flow from the inflow portion 12 into the sand settling portions 14a, 14b, 14c.

At an exit of the sand basin 10, removal pumps 16 are arranged. The removal pumps 16 move the disinfected wet-weather sewage to a discharge waterway 17. Then, the wet-weather sewage in the discharge waterway 17 is measured by a measuring instrument 18 such as a residual halogen detector, a turbidimeter, or an electrical conductivity meter. The residual halogen detector measures the residual concentration of an active halogen such as hypobromous acid. Thus, it is usually preferred that the residual halogen detector be disposed behind the exit of the sand basin and forward of a discharge port.

If the active halogen concentration detected by the residual halogen detector is not less than $LC_{50}$ (in the case of BCDMH, for example, 0.4 mg/liter calculated as active chlorine ($Cl_2$)), the amount of the disinfectant or the disinfecting water supplied is decreased, or the supply of the disinfectant or the disinfecting water is temporarily cut off, so that the active halogen concentration will be lower than $LC_{50}$. Desirably, if the active halogen concentration is not less than a half of $LC_{50}$ (in the case of BCDMH, for example, 0.2 mg/liter calculated as active chlorine ($Cl_2$)), the same measure as above is taken, so that the active halogen concentration will be lower than a half of $LC_{50}$. By this measure, adverse influence on aquatic organisms in public waters can be reduced.

After the measured values and the coliform organism count of the disinfected wet-weather sewage have been confirmed to fulfill the predetermined discharge standards, the disinfected wet-weather sewage is discharged to public waters such as rivers.

The public waters include rivers, lakes, ports, coastal waters, public drains, irrigation waterways, and waters or waterways for public use. However, the public waters do not include sewers, especially, sewers having wastewater treatment plants downstream.

According to the embodiment of FIG. 1, a bypass channel 20 is connected to the inflow portion 12 of the sand basin 10. Part of the wet-weather sewage that has flowed into the inflow portion 12 of the sand basin 10 is introduced into the bypass channel 20. To this partial wet-weather sewage, the disinfectant is added to convert it to disinfecting water, which is returned to the sand basin 10.

In the inflow portion 12 of the sand basin 10, a bucket pump 13 is disposed. Part of the wet-weather sewage in the inflow portion 12 is lifted to the bypass channel 20 by the bucket pump 13. The other portion of the wet-weather sewage in the inflow portion 12 flows into the sand setting portions 14a, 14b, 14c.

In the bypass channel 20, a pair of automatic screens 22a, 22b, a flow meter 23, a disinfectant adding device 30, a dissolving device 40, pumps 46, and a distribution tank 48 are disposed in this order. The automatic screens 22a and 22b are arranged parallel to each other.

The disinfectant adding device 30 has a hopper 32 for storing a disinfectant 39, a feeder 34 for feeding the disinfectant 39, and an ejector 36 for discharging the disinfectant to the channel.

The wet-weather sewage having the disinfectant added thereto is guided to the device 40. The device 40 dissolves the disinfectant in the wet-weather sewage, when the disinfectant is a solid. The device 40 mixes the disinfectant with the wet-weather sewage, when the disinfectant is a liquid. The device 40 has a tank 41, which, according to the embodiment of FIG. 1, is divided into an agitation tank 41a and a storage tank 41b, although the tank 41 need not be divided into two tanks.

The agitation tank 41a has a water level gauge 42, and a stirrer 44 for stirring drainage. The stirrer 44 has, for example, a motor 44a, a shaft 44b connected to the motor 44a, and a stirring tool 44c fixed to the shaft, such as a vane or an impeller. The drainage in the agitation tank 41a is stirred with the stirrer 44, so that the solid disinfectant in the drainage can be dissolved. The drainage that has overflowed from the agitation tank 41a is moved into the storage tank 41b.

When the solubility of the solid disinfectant is low, it is preferred to provide the dissolving device 40. When the solubility of the solid disinfectant is high, the dissolving device 40 is not absolutely necessary, because the disinfectant dissolves rapidly in the channel.

Disinfecting water obtained in the device 40 is guided to the sand basin 10 via a channel 47 preferably by means of the pumps 46. The disinfecting water may be guided directly to the sand basin 10 as shown in FIG. 1, or may be guided to the sand basin 10 via the distribution tank 48 as shown in FIG. 2.

Figure 2:
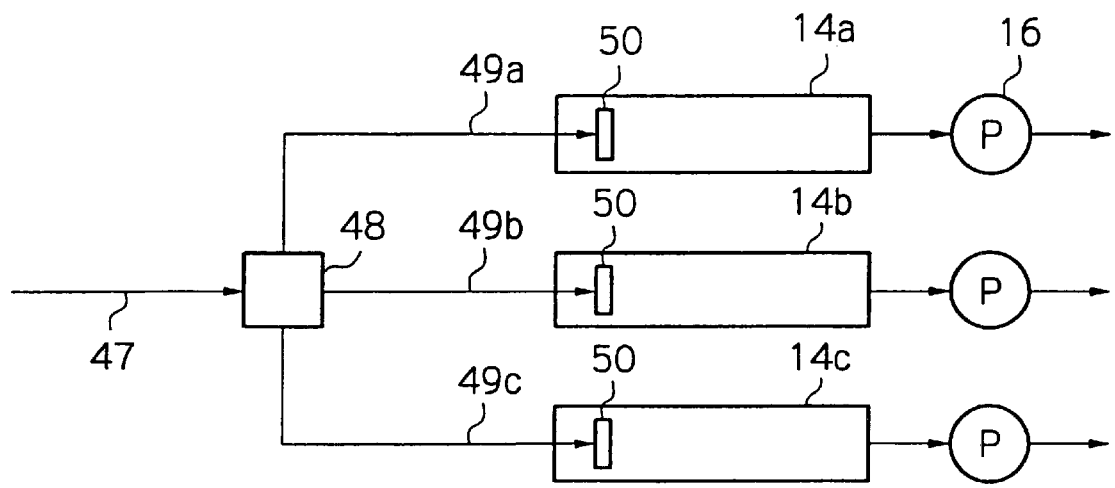
FIG. 2 is an explanatory view of a portion of another embodiment of the apparatus according to the invention.

In FIG. 2, the distribution tank 48 is provided in the channel 47. In FIG. 2, the sand settling portions 14a, 14b, 14c of the sand basin 10 are illustrated, and the inflow FIG. 15 portion 12 is omitted, for convenience of explanation.

The disinfecting water may be guided to the inflow portion 12 of the sand basin 10 as shown in FIG. 1, or may be introduced upstream of each of the sand settling portions 14a, 14b, 14c of the sand basin 10.

As shown in FIG. 2, when the disinfecting water is introduced upstream of each of the sand settling portions 14a, 14b, 14c of the sand basin 10, the disinfecting water to be guided to each of the sand settling portions 14a, 14b, 14c is preferably distributed at the distribution tank 48 beforehand.

In the sand settling portions 14a, 14b, 14c, sand included in the wet-weather sewage is sedimented and removed. Simultaneously, the wet-weather sewage and the disinfecting water mix to disinfect the wet-weather sewage. In the sand settling portions 14a, 14b, 14c, the wet-weather sewage and the disinfecting water dwell preferably for 1 second to 30 minutes, more preferably for 1 second to 15 minutes, and most preferably for 1 second to 10 minutes.

Figure 3:
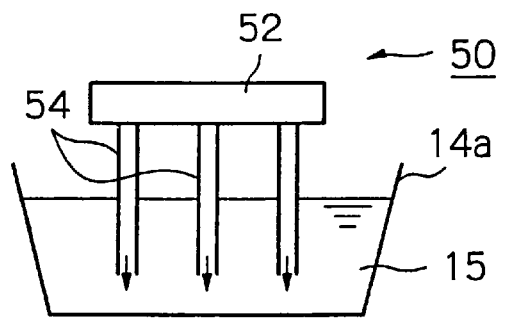
FIG. 3 is a sectional view of an embodiment of a device which can be used in the invention.

FIG. 3 shows an embodiment of an adding device for adding the disinfecting water to the sand settling portion. An adding device 50 has a pipe 52 extending in a horizontal direction, and an introducing portion communicating with this pipe 52 for introducing the disinfecting water into drainage. The pipe 52 is connected to a channel 49a, and supported by a support member (not shown). An embodiment of the introducing portion is, for example, a plurality of hoses 54 suspending from the pipe 52. An open end 56 of the hose is preferably located at an upstream position of the sand settling portion 14a, and located below the water surface. The disinfecting water distributed from the distribution tank 48 flows in the channel 49a, the pipe 52, and the hose 54 in this order, and added to drainage 15 in the sand settling portion 14a.

If the open end 56 of the hose 54 is located above the water surface of the drainage 15 in the sand settling portion 14a, splashes of the disinfecting water from the open end 56 of the hose may form a mist with the wind or the like, corroding instruments around the sand basin 10, especially, electrical instruments. The open end 56 of the hose is preferably located below the water surface of the drainage 15 in the sand settling portions 14a, 14b, 14c.

The pipe 52 is preferably made of a material which is not corroded with the disinfecting water. Its examples are metallic materials such as inconel, and plastic materials such as polytetrafluoroethylene, and polyvinyl chloride. The pipe 52 preferably has sufficient mechanical strength to support the hoses. Preferably, it is rigid, but may be flexible.

From each pipe 52, 2 to 20 hoses, preferably 2 to 10 hoses, more preferably 2 to 6 hoses, may be suspended. The distance between the two adjacent hoses is preferably constant, because the disinfecting water can be mixed with the drainage efficiently. However, the distance between the two adjacent hoses may be different. The hose 54 is preferably flexible, but may be rigid.

EXAMPLES

Examples of the present invention will now be described, but the invention is not restricted thereby. In the following Examples, drainage was treated by the system shown in FIGS. 1 to 3.

Example 1

Treated sewage containing coliform organisms, as water to be treated, was subjected to a sterilization test. As a disinfectant, each of 1-bromo-3-chloro-5,5-dimethylhydantoin (hereinafter referred to as BCDMH) (Example 1) and sodium hypochlorite (Comparative Example 1) was used. The sterilization test of coliform organisms was conducted, with the concentration of the disinfectant being varied. The water quality of the water to be treated is shown in Table 1.

TABLE 1

| Item analyzed | Measured value |
| --- | --- |
| Turbidity | 14 mg/L |
| SS | 9 mg/L |
| COD | 17 mg/L |
| Chromaticity | 22 mg/L |
| $NH_4$-N | 22 mg/L |
| Coliform organism count | 12600 CFU/mL |
| TOC | 9 mg/L |

TABLE 2

| Disinfectant used | Concentration of disinfectant added (mg/L as Cl) | Coliform organism count (CFU/mL) |
| --- | --- | --- |
| None | 0 | 12600 |
| BCDMH | 0.5 | 10800 |
|  | 1.0 | 2300 |
|  | 1.5 | 70 |
|  | 2.0 | Not detected |
| Sodium hypochlorite | 2.0 | 11800 |
|  | 2.5 | 2800 |
|  | 3.0 | 300 |
|  | 3.5 | Not detected |

BCDMH exhibited a germicidal effect at a concentration of a half or less of the concentration of sodium hypochlorite, and decreased the coliform organism count to less than 3,000 CFU/mL when added in a concentration of 1 mg/L as Cl.

When BCDMH was added in an amount of 1 mg/L as Cl, trihalomethane remained in an amount of 0.1 mg/L or less.

In the present specification, the proportion of the disinfectant added is expressed as active chlorine for each of the bromine-based disinfectant and the chlorine-based disinfectant, and is expressed as "mg/L as Cl" calculated as the active chlorine concentration. For example, when 1 g of BCDMH is added to 1 liter of drainage, its concentration is 540 mg/L as Cl.

As for the reaction time, BCDMH showed a sufficient effect in 1 minute, while sodium hypochlorite required a reaction time of more than 5 minutes to show its effect.

Example 2

Drainage from the marine product processing industry was subjected to coagulation, pressurization, floating, and separation. Then, the drainage was further treated by an activated sludge process. The resulting drainage was used as water to be treated. A sterilization test of this water to be treated was conducted, with the concentration of a disinfectant being varied. The water quality of the water to be treated is shown in Table 3, and the test results are shown in Table 4.

TABLE 3

Water quality of drainage from marine product processing after waste water treatment

| Item analyzed | Measured value |
| --- | --- |
| SS | 42 mg/L |
| COD | 230 mg/L |
| $NH_4$-N | 143 mg/L |
| Organic nitrogen | 104 mg/L |
| Coliform organism count | 320000 CFU/mL |
| TOC | 78 mg/L |

The organic nitrogen refers to the value of the total organic nitrogen, including amines and protein. In the case of protein, for example, the organic nitrogen refers to the amount of the nitrogen atoms in the protein, and does not include the amounts of the carbon atoms or hydrogen atoms in the protein. The organic nitrogen does not include inorganic nitrogen, such as that in ammonia or ammonium ions.

TABLE 4

| Disinfectant used | Germicidal effect | |
|---|---|---|
| | Concentration of disinfectant added (mg/L as Cl) | Coliform organism count (CFU/mL) |
| BCDMH | 0 | 320000 |
| | 2.0 | 52000 |
| | 2.5 | 2800 |
| | 3.0 | 1200 |
| | 3.5 | Not detected |
| Sodium hypochlorite | 6 | 135000 |
| | 8 | 1900 |
| | 10 | 900 |
| | 12 | Not detected |

BCDMH exhibited a genermicidal effect at a concentration of ⅓ or less of the concentration of sodium hypochlorite, and decreased the coliform organism count to less than 3,000 CFU/mL when added in a concentration of 2.5 mg/L as Cl.

Example 3

Drainage was treated by the system show in FIGS. 1 to 3. The results are shown in Table 5.

TABLE 5

| | | Disinfectant | | | | | | |
|---|---|---|---|---|---|---|---|---|
| | Amount of sewage [m³/h] | Type (*1) | Amount added (*2) [mg/l] | Coliform organism count [CFU/ml] | Residual halogen [calc'd. as chlorine (Cl₂)] [mg/l] | Turbidity [degree] | Electrical conductivity [µS/cm] | TOC [mg/l] | NH₄—N [mg/l] |
| RUN 1 | 120 | — | 0 | 97 × 10³ | ND (*3) | 75 | 825 | 72 | 17.4 |
| | 120 | A | 6.0 | 83 × 10² | ND | 78 | 835 | | |
| | 120 | A | 12.0 | 12 × 10 | 0.18 | 76 | 810 | | |
| RUN 2 | 250 | — | 0 | 68 × 10³ | ND | 52 | 485 | 47 | 4.3 |
| | 250 | A | 5.0 | 18 × 10² | 0.03 | 57 | 472 | | |
| | 250 | A | 10.0 | 20 or less | 0.72 | 48 | 460 | | |
| RUN 3 | 530 | — | 0 | 39 × 10³ | ND | 37 | 248 | 40 | 3.5 |
| | 530 | A | 3.0 | 28 × 10² | ND | 32 | 261 | | |
| | 530 | A | 4.5 | 17 × 10 | 0.12 | 39 | 273 | | |
| RUN 4 | 250 | — | 0 | 46 × 10³ | ND | 49 | 420 | 60 | 6.9 |
| | 250 | B | 30 | 19 × 10³ | ND | 48 | 428 | | |
| | 250 | B | 60 | 41 × 10² | 1.53 | 46 | 415 | | |

(*1): A represents BCDMH (available halogen concentration 54%).
B represents sodium hypochlorite (available halogen concentration 10%).
(*2): Amount added, calculated as chlorine (Cl₂) [mg/l].
(*3): ND denotes "Not Detected".

In RUN 1 (amount of sewage: 120 m³/hour), the coliform organism count could be decreased to less than 3,000 CFU/ml then the amount of BCDMH added was 12 mg/l.

In RUN 2 (amount of sewage: 250 m³/hour), when the amount of BCDMH added was 10 mg/l, disinfection was sufficient, but the residual halogen concentration was 0.72 mg/l, which was not appropriate. When the amount of BCDMH added was 5 mg/l, the coliform organism count could be decreased to less than 3,000 CFU/ml, and the residual halogen concentration was 0.03 mg/l. This was appropriate.

RUN 3 (amount of sewage: 530 m³/hour) corresponds to a large rainfall. In this case, appropriate disinfection was possible when the amount of BCDMH added was 3 to 4.5 mg/l. On this occasion, the duration of contact of BCDMH with combined sewer overflow was found to be about 50 seconds, meaning successful disintegration in a very short time.

At RUN 4 (amount of sewage: 250 m³/hour) is a comparative example in which sodium hypochlorite was used as the chlorine-based disinfectant. In RUN 4, even when the amount of sodium hypochlorite added was 60 mg/l, the coliform organism count could not be decreased to 3,000 CFU/ml or less, and the residual halogen concentration was 1.53 mg/l, a higher value than $LC_{50}$ (concretely, 0.4 mg/l calculated as chlorine ($Cl_2$)). This is inappropriate.

In all of RUN 1 to RUN 4, the amount of the disinfectant being 0 (zero) corresponds to the incoming water quality of wet-weather sewage which has flowed into rainwater removal facilities.

According to the present invention, drainage such as wet-weather sewage can be disinfected efficiently. Furthermore, disinfection is possible, even when the residual halogen concentration is less than 0.4 mg/l, the $LC_{50}$ value. By detecting the residual halogen concentration, moreover, the amount of the disinfectant or disinfecting water supplied can be decreased, or the supply of the disinfectant or disinfecting water can be cut off, if the detected value exceeds the control value of the residual halogen concentration. Thus, consideration for the environment can be taken.

What is claimed is:

1. A method comprising
   adding a disinfectant to water to obtain a disinfecting water, said disinfectant capable of forming HOX wherein X is a bromine atom or an iodine atom,
   wherein said disinfectant comprises a heterocyclic compound containing in a cyclic structure a moiety of the formula:

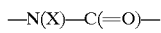
   —N(X)—C(=O)— wherein X is the same as above; and
   adding the disinfecting water to a drainage comprising organic matter and ammonia or ammonium ions, to disinfect the drainage.

2. The method of claim 1, wherein said disinfectant is a 4- to 10-membered heterocyclic ring which contains 1 to 4 hetero atoms selected from the group consisting of nitrogen and sulfur.

3. The method of claim 1, wherein the disinfectant is a solid, and obtaining disinfecting water includes dissolving the disinfectant in the drainage.

4. The method of claim 1, wherein the concentration of the disinfectant in the disinfecting water is of from 100 mg/liter to 10 mg/liter as Cl calculated in terms of active chlorine concentration.

5. The method of claim 1, wherein the concentration of the disinfectant added in the drainage is of from 0.5 mg/liter to 25 mg/liter as Cl calculated in terms of active chlorine concentration.

6. The method of claim 1, wherein the molar ratio of XOH, to the concentration of ammonium ion is not more than 1.5.

7. The method of claim 1, wherein the contacting time of the disinfecting water with the drainage is not more than 5 minutes.

8. The method of claim 1, wherein adding the disinfecting water to the drainage includes introducing the disinfecting water below a water surface of the drainage.

9. The method of claim 1, wherein the disinfectant is added to a storm pump room, a storm overflow chamber or a wet-weather sewer overflow waterway.

10. The method of claim 1, wherein the total organic carbon of the drainage is more than 5 mg/liter.

11. The method of claim 1, wherein the concentration of ammonium ion is more than 1 mg/liter.

12. The method of claim 1, wherein the drainage contains rainwater.

13. The method of claim 1, wherein the drainage comprises sewage diluted with rainwater.

14. The method of claim 1, wherein the drainage is wet-weather overflow water.

15. The method of claim 1, further comprising discharging the disinfected drainage to public waters.

16. An apparatus comprising a disinfecting water-producing device, a first channel and a sand basin,
wherein the first channel connects the disinfecting water-producing device and the sand basin, and
wherein the disinfecting water-producing device comprises a disinfectant storing device, an adding device and a mixing device.

17. The apparatus of claim 16, further comprising a reservoir or a discharge waterway.

18. The apparatus of claim 17, further comprising a measuring instrument, wherein said measuring instrument is present in the reservoir or a discharge waterway.

19. The apparatus of claim 16, further comprising a second channel, wherein the second channel connects the sand basin and the disinfecting water-producing device.

20. The apparatus of claim 16, wherein the sand basin comprises two or more sand settling portions, and the first channel is connected to each of the sand settling portions through one or more distribution tanks.

21. An apparatus comprising a disinfecting water-producing device, a first channel, and a sand basin,
wherein the first channel connects the disinfecting water-producing device and the sand basin, and
wherein the first channel is connected to an adding device.

* * * * *